US 9,759,694 B2

United States Patent
Tanoue et al.

(10) Patent No.: US 9,759,694 B2
(45) Date of Patent: Sep. 12, 2017

(54) LIQUID CHROMATOGRAPH APPARATUS AND LIQUID CHROMATOGRAPH ANALYSIS METHOD

(71) Applicant: Hitachi High-Technologies Corporation, Tokyo (JP)

(72) Inventors: Toyoaki Tanoue, Tokyo (JP); Masato Fukuda, Tokyo (JP); Daisuke Akieda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 589 days.

(21) Appl. No.: 14/251,823

(22) Filed: Apr. 14, 2014

(65) Prior Publication Data

US 2014/0311228 A1     Oct. 23, 2014

(30) Foreign Application Priority Data

Apr. 18, 2013  (JP) ................................. 2013-087039

(51) Int. Cl.
*G01N 30/24* (2006.01)
*G01N 30/32* (2006.01)

(52) U.S. Cl.
CPC ............ *G01N 30/24* (2013.01); *G01N 30/32* (2013.01)

(58) Field of Classification Search
CPC ................................ G01N 30/24; G01N 30/32
See application file for complete search history.

(56) References Cited

U.S. PATENT DOCUMENTS

| | | | | |
|---|---|---|---|---|
| 3,960,003 A | * | 6/1976 | Beyer ..................... | G01N 30/24 73/61.56 |
| 2009/0062966 A1 | | 3/2009 | Pensak, Jr. et al. | |
| 2009/0090173 A1 | * | 4/2009 | Fukuda ................... | G01N 30/34 73/61.55 |
| 2009/0205409 A1 | * | 8/2009 | Ciavarini ............... | G01N 30/34 73/61.56 |
| 2011/0202188 A1 | | 8/2011 | Pensak, Jr. et al. | |
| 2012/0303167 A1 | * | 11/2012 | Heden .................... | G01N 30/24 700/282 |

FOREIGN PATENT DOCUMENTS

| | | |
|---|---|---|
| JP | 07-072130 A | 3/1995 |
| JP | 2006-017590 A | 1/2006 |
| JP | 2008-511002 A | 4/2008 |
| JP | 2012-058264 A | 3/2012 |
| WO | 03/079000 A1 | 9/2003 |

\* cited by examiner

*Primary Examiner* — Hezron E Williams
*Assistant Examiner* — David Z Huang
(74) *Attorney, Agent, or Firm* — Mattingly & Malur, PC

(57) ABSTRACT

An analysis method is achieved in which pressure variation resulting from sample injection or passage switching by an autosampler does not exert an influence on the control of a liquid transfer pump. The liquid chromatograph analysis method comprises the steps of: transferring two or more types of eluents while changing a mixing ratio between the eluents; adjusting an amount of the transferred liquid within a predetermined time in a passage for the eluent transferred; injecting a sample in the passage; supplying to a separation column the eluent into which the sample is injected; separating a target component in the sample; and detecting the target component thus separated. In this method, control is exercised so as to synchronize a liquid transfer cycle of the eluent with the sample injecting operation and to implement the sample injecting operation at a timing rather than the pressure obtaining time.

11 Claims, 12 Drawing Sheets

FIG. 8
~DURING THE CONNECTION OF A SAMPLE INTRODUCTION PASSAGE~
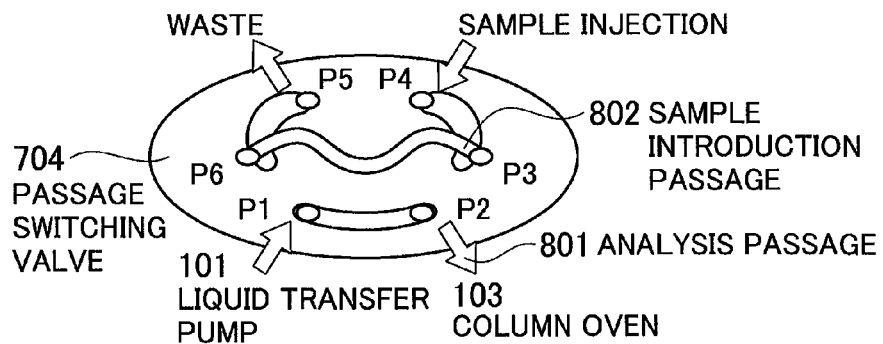
~AT THE TIME OF PASSAGE SWITCHING~
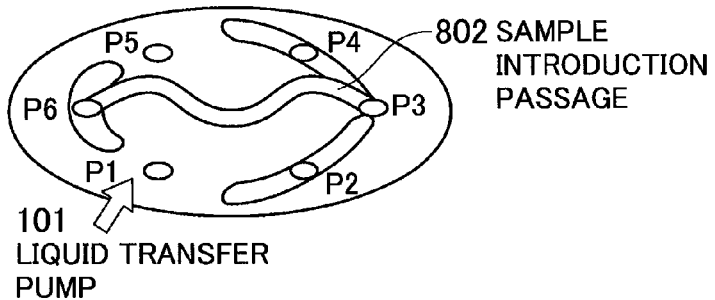
~DURING THE CONNECTION OF THE ANALYSIS PASSAGE~
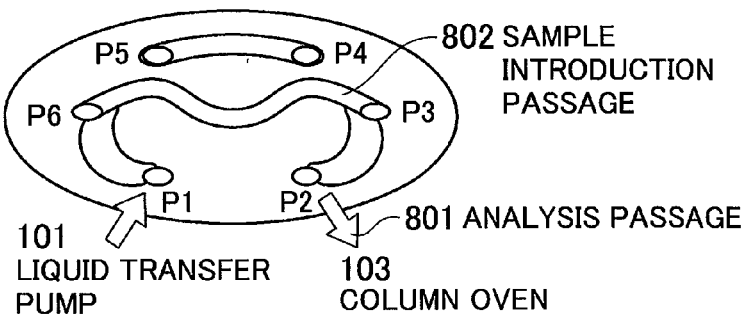

LIQUID CHROMATOGRAPH APPARATUS AND LIQUID CHROMATOGRAPH ANALYSIS METHOD

BACKGROUND OF THE INVENTION

1. Field of the Invention

The present invention relates to a liquid chromatograph apparatus and a liquid chromatograph analysis method.

2. Description of the Related Art

For analyses in which a liquid chromatograph apparatus is used, a plurality of components in a sample are detected by means of a gradient method which mixes a plurality of eluents and allows their concentration to change during analysis. The gradient method uses a plurality of liquid transfer devices different in liquid transfer velocity to make it possible to prepare a targeted mixing concentration on the basis of a difference between their velocities.

To improve the degree of reproducibility of analysis, JP-2012-58264-A (hereinafter referred to as Patent Document 1) discloses a technology which includes means for transmitting to an autosampler or a control unit the fact that a plurality of pumps reach the given timing of a liquid transfer cycle. In addition, the technology promotes synchronization with an analysis cycle by transmitting information on a pump whose liquid transfer cycle is slowest to the autosampler or the control unit.

JP-2006-17590-A (hereinafter referred to as Patent Document 2) describes switching from a start operation mode to a steady operation mode. In the start operation mode, one of two pumps is operated in order to reduce a rise time at the time of starting the pump. In the steady operation mode, after the discharge pressure of fluid has reached a predetermined value, the pump which has been operated is stopped and the other pump is operated.

JP-7-72130-A (hereinafter referred to as Patent Document 3) discloses determining a timing at which supply of fluid into a system is started, by monitoring a fluid compression process and detecting the system pressure being obtained precisely.

International Publication No. WO2003/079000 (hereinafter referred to as Patent Document 4) discloses a high-pressure gradient liquid transfer method, specifically, a method of controlling the rotational speed of a motor on the basis of the position of a cam for operating the motor and a differential value between pressures in a plurality of pumps.

JP-T-2008-511002 (hereinafter referred to as Patent Document 5) discloses the fact that to suppress a decrease in fluid pressure resulting from the injection of a sample, the operation of a pump is controlled before or during the injecting operation to change the pressure.

SUMMARY OF THE INVENTION

Liquid transfer devices which perform long-time liquid transfer need a process for sucking an eluent and a process for discharging it. It is ideal that transferred liquid will be controlled to keep a fixed pressure depending on preset conditions, including a connection interval between the processes; however, practically, the pressure of transferred liquid is changeable due to the various causes.

Some of the causes, such as injection of a sample into a passage and switching of a passage, can temporarily change the pressure of transferred liquid along with a predetermined operation in an analysis cycle.

In the methods described in Patent Documents 1 to 5, the pressure of transferred liquid would thus be temporarily changed due to sample injection into a passage, switching of a passage, and others. If the liquid transfer device is controlled on the basis of the transferred liquid pressure, which has changed in this way, then an accurate analysis result is not obtained in some times.

It is an object of the present invention to provide a liquid chromatograph apparatus and a liquid chromatograph analysis method that can suppress an influence of pressure variation resulting from the injection of a sample into a transferred fluid or the switching of a passage, thereby implementing analysis with a high degree of accuracy and reproducibility.

According to one aspect of the present invention, there is provided a liquid chromatograph apparatus comprising: a liquid transfer pump for transferring liquid; an autosampler for injecting a sample in the liquid transferred in a passage and switching the passage; a pressure obtaining section for obtaining pressure in the passage; and a control section for controlling an amount of the liquid transferred on the basis of the pressure obtained, wherein the control section controls the autosampler so that the liquid transfer cycle of the liquid transfer pump and sample injecting operation may be synchronized with each other and the sample injecting operation may be implemented at a timing rather than an interval in which pressure is obtained by the pressure obtaining section.

According to another aspect of the present invention, there is provided a method using the liquid chromatograph apparatus described above.

The above aspects of the present invention can suppress an influence of a variation in liquid transfer pressure resulting from the sample injection or the passage switching operation on analysis results and can implement analysis with a high degree of accuracy and of reproducibility.

BRIEF DESCRIPTION OF THE DRAWINGS

FIG. 8 illustrates the configurations of a passage switching valve in respective processes according to an embodiment of the present invention.

DESCRIPTION OF THE PREFERRED EMBODIMENTS

Preferred embodiments of the present invention will hereinafter be described with reference to the drawings.

A liquid chromatograph apparatus including a chromatograph unit and a data processing unit for controlling the chromatograph unit is exemplified as a configuration which can best describe the embodiment of the present invention. The chromatograph unit includes a liquid transfer pump A, a liquid transfer pump B, an autosampler, a column oven and a detector in FIG. 1.

Figure 1:
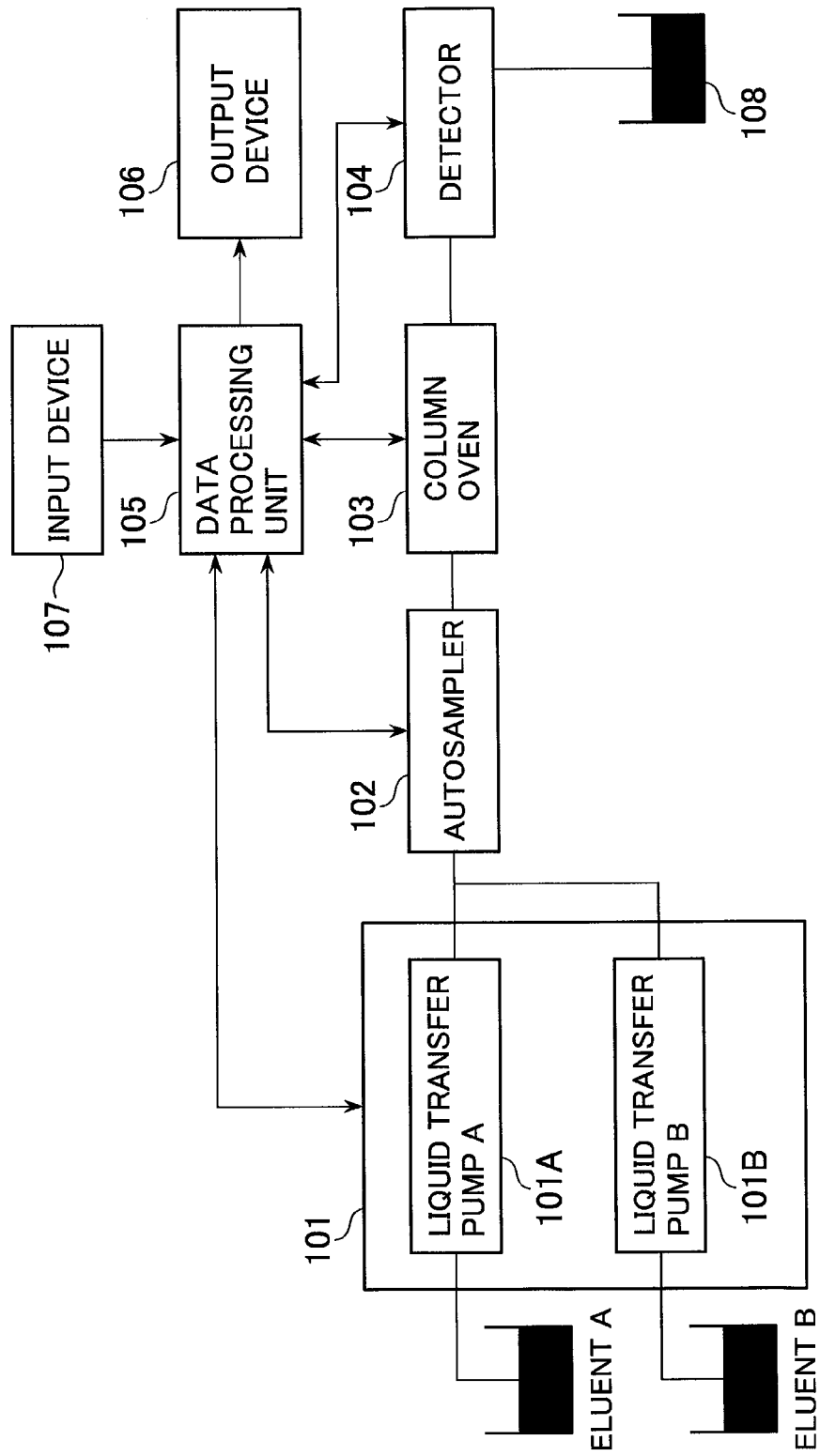
FIG. 1 illustrates a configuration of a liquid chromatograph apparatus which uses a plurality of liquid transfer pumps to mix eluents according to an embodiment of the present invention.

FIG. 1 is a diagram illustrating the configuration of the liquid chromatograph apparatus according to the present embodiment. An eluent A and an eluent B are sucked by the liquid transfer pump 101A and the liquid transfer pump 101B, respectively, mixed with each other, and then transferred to the column oven 103 via the autosampler 102.

Figure 12:
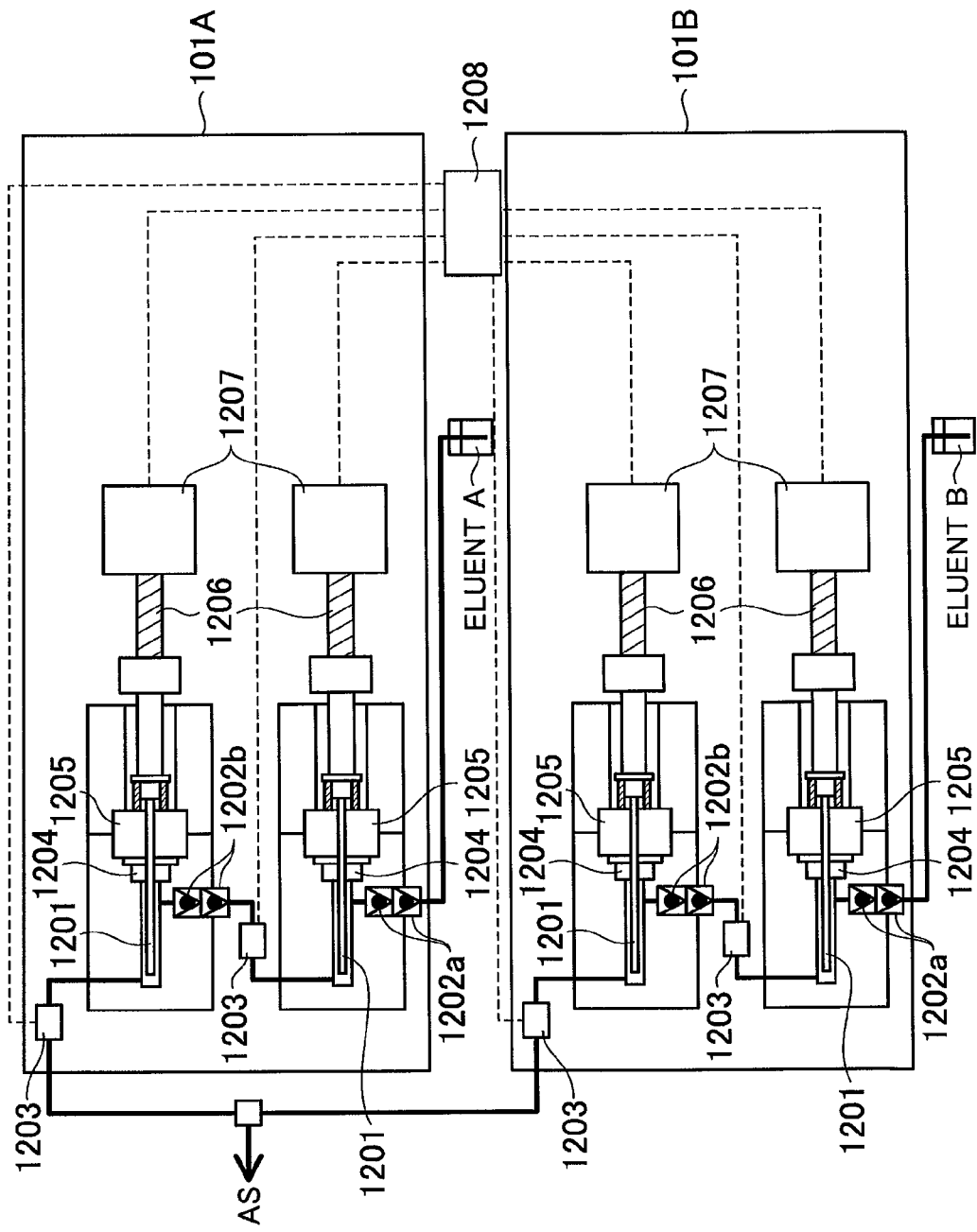
FIG. 12 illustrates the configuration of the liquid transfer pump according to the embodiment of the present invention.

In addition, the liquid transfer pump is here described. FIG. 12 illustrates the configuration of the liquid transfer pump according to an embodiment of the present invention.

The liquid transfer pump according to the embodiment consists of two pump units. Each pump unit includes one cylinder, a plunger 1201 provided in association with the cylinder, a check valve 1202, a pressure sensor 1203, a plunger seal 1204; a plunger guide 1205, an actuator 1206 for the plunger, and a motor 1207. The cylinder is here referred to a single cylinder provided with the associated plunger and plunger seal.

Drive force driving the plunger 1201 is derived from the motor 1207. The rotational movement of the motor 1207 is converted into translatory movement by the actuator 1206 and the translatory movement is transmitted to the plunger 1201.

The pressure of the eluent transferred is detected by the pressure sensor 1203 provided on the side where fluid is discharged by the plunger 1201. The detection result of the pressure sensor 1203 is sent to the data processing unit 105 shown in FIG. 1 via a liquid transfer control section 1208.

The liquid transfer control section 1208 controls the operations of the liquid transfer pumps 101A and 101B solely or through exchange of signals with the data control section 105 shown in FIG. 1.

Specifically, the liquid transfer pumps 101A and 101B are controllably driven by the liquid transfer control section 1208 using liquid transfer pressure. In this case, liquid transfer conditions such as a liquid transfer flow rate and the like are set by receiving instruction signals from the data processing unit 105.

A sample injected by the autosampler 102 is delivered to the column oven 103 along with a mixed liquid of the eluents transferred by the liquid transfer pumps 101A and 101B. The sample is separated into components by the column oven 103. The column oven 103 has a separation column whose temperature is maintained at a fixed temperature by the column oven 103.

The separated components are detected by the detector 104 and discarded into a waste container 108. The measurement values of the components detected by the detector 104 are taken into the data processing unit 105, which obtains the height and area of a chromatogram peak. Their results are indicated on the output device 106 such as a display or the like.

The input device 107 such as a keyboard, a mouse or the like is connected to the data processing unit 105. The input device 107 is used to input the setting of device configuration information and of analysis conditions. The data processing unit 105 controls the autosampler 102 to control the injecting amount of a sample and also controls the temperature of the column oven 103.

Figure 9:
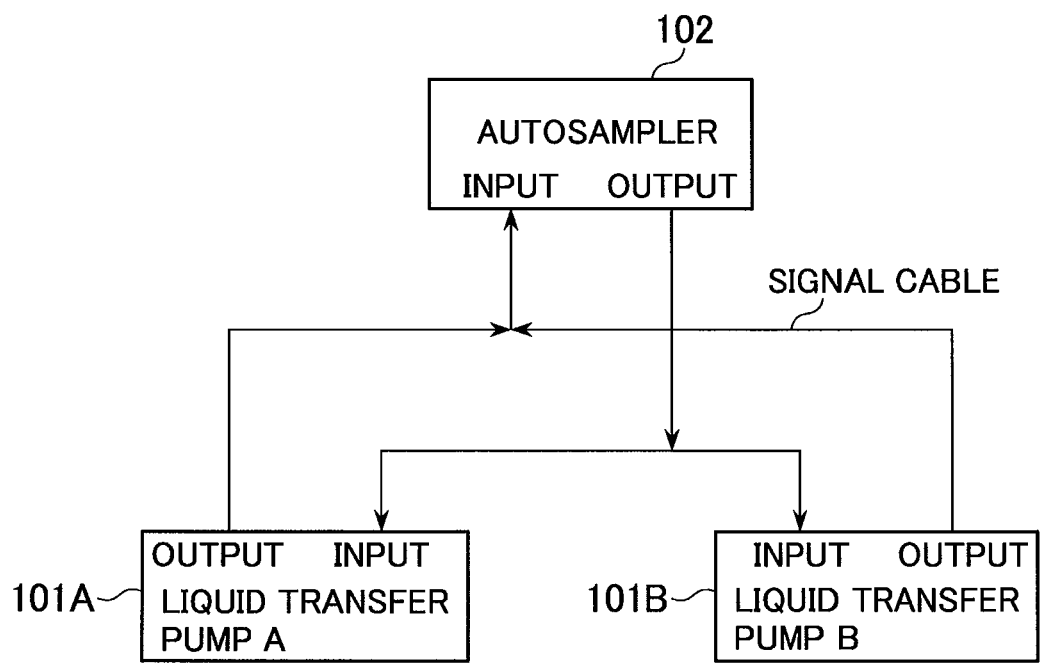
FIG. 9 illustrates connection of signal cables of the liquid transfer pumps and the autosampler according to an embodiment of the present invention.
Figure 10:
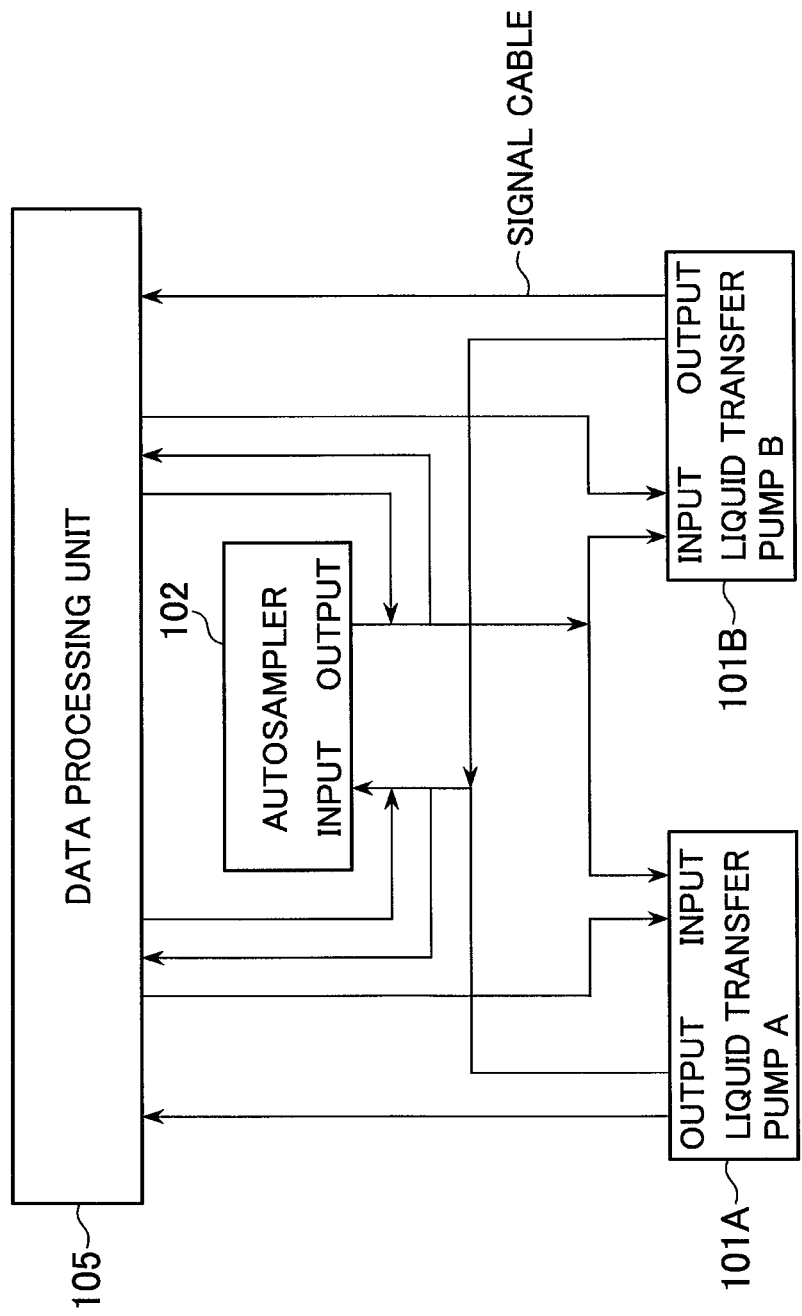
FIG. 10 illustrates connection of signal cables of the liquid transfer pumps, the autosampler and the data processing unit according to an embodiment of the present invention.

As shown in FIG. 9, the liquid transfer pump 101 and the autosampler 102 are connected so as to be able to communicate with each other by means such as signal cables or the like. An electric signal as hardware and communication means as software are applicable as this means. Specifically, both of the liquid transfer pump 101 and the autosampler 102 can output a synchronization signal. An output signal is sent from one of the liquid transfer pump 101 and the autosampler 102 to the other with one of their cycles matched with the other. In this way, the operations of the liquid transfer pump 101 and the autosampler 102 can be synchronized with each other.

Further, as described later in a third embodiment, signal cables or the like are connected to the data processing unit 105 so that even the data processing unit 105 may detect signals outputted from the liquid transfer pumps 101A and 101B and the autosampler 102. In this way, the data processing unit 105 can receive such signals.

Figure 7:
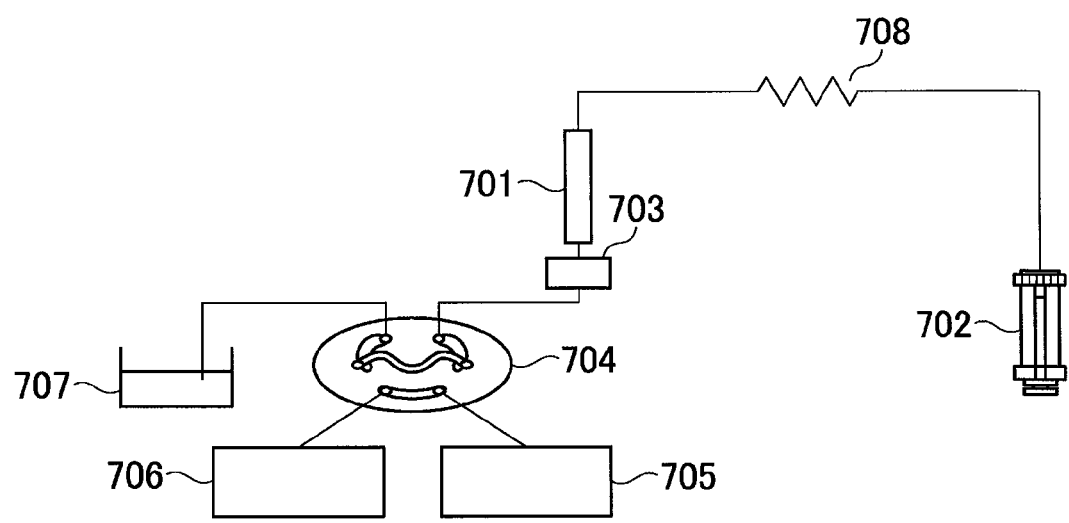
FIG. 7 illustrates an overall configuration of an autosampler according to an embodiment of the present invention.

The autosampler 102 is next described with reference to FIG. 7. A sample is measured by a syringe 702 via a needle 701. The needle 701 is connected to an injecting port 703. The sample is injected toward a passage switching valve 704.

The sample thus injected is introduced into a sample introduction passage in the passage switching valve 704. By switching the passage switching valve 704, the sample introduction passage is switched to an analysis passage (downstream of a column 705), so that the sample is introduced toward the column.

FIG. 8 illustrates the positional configurations of the passage switching valve 704 during the connection of the sample introduction passage, at the time of switching of the passage and during the connection of the analysis passage. As illustrated in FIG. 8, grooves provided in a valve body are connected to the sample introduction passage 802, from this state the valve body is turned to perform a switching operation, and the groove is connected to the analysis passage 801. The passage switching valve 704 is such that the grooves are temporarily blocked during the switching operation (for about 100 to 300 ms); therefore, no liquid flows into the analysis passage 801 from the side of the liquid transfer pump 101. Immediately after the connection with the analysis passage 801, liquid flows into the analysis passage 801 with the pressure of the liquid increased.

Figure 2:
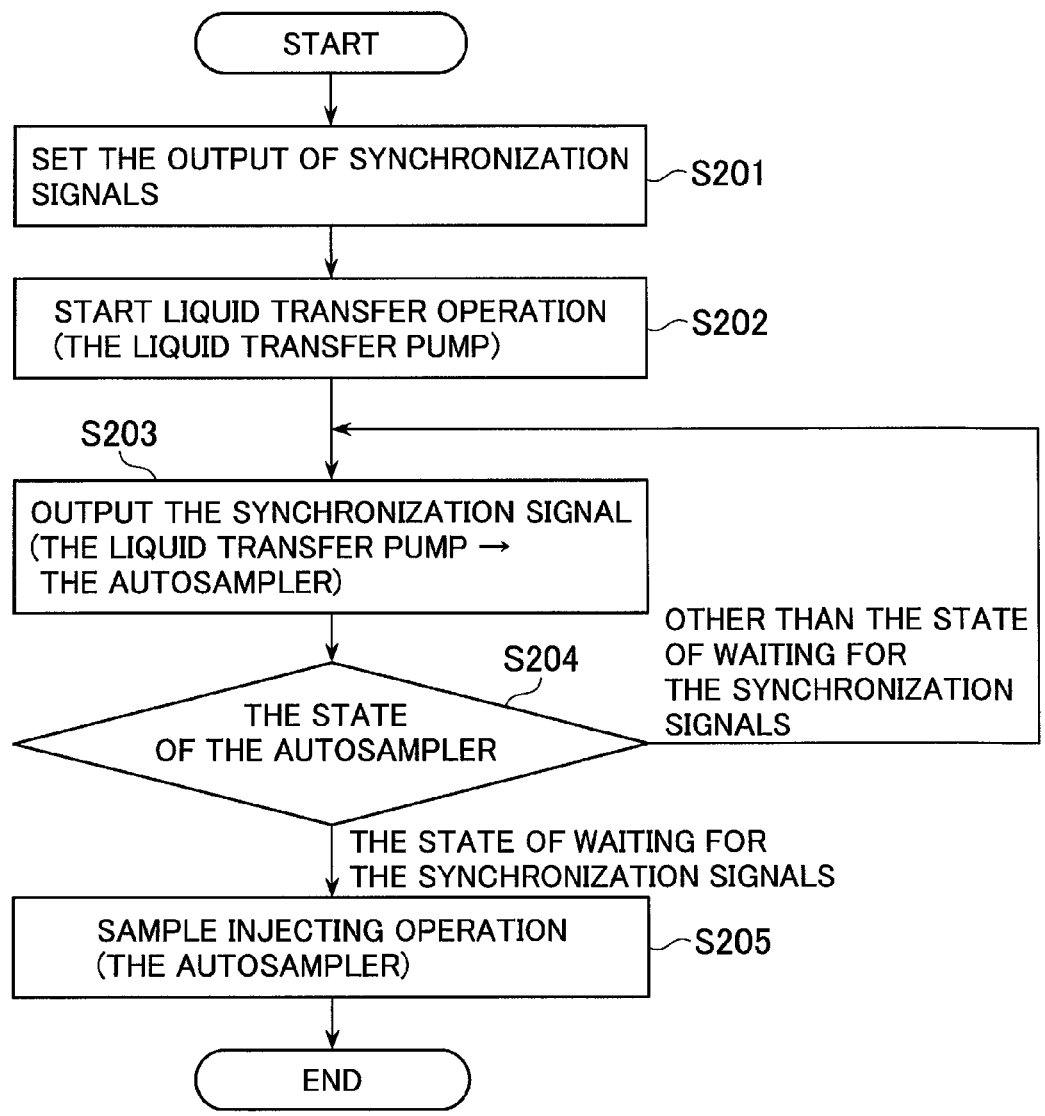
FIG. 2 is a conventional operation flowchart.

FIG. 2 is a conventional flowchart for illustrating the sample injecting operation of the autosampler 102 synchronous with the output signal from the liquid transfer pump 101.

The output of the respective synchronization signals from the liquid transfer pumps 101A and 101B is set so as to control the timing of the sample injecting operation of the autosampler 102 (S201).

The liquid transfer pumps 101A and 101B start liquid transfer operation (S202). The liquid transfer pumps 101A and 101B output respective synchronization signals to the autosampler 102 on the basis of respective liquid transfer cycles (S203). The synchronization signal is a signal which instructs the autosampler 102 to permit sample injection and passage switching operation.

If the autosampler 102 is in the state of waiting for the synchronization signals (S204), the autosampler 102 implements the sample injecting operation on the basis of the signals outputted from the liquid transfer pumps (S205). Here, the state of waiting for the synchronization signals means a state where for example, the needle 701 and passage switching valve 704 of the autosampler lie at respective predetermined positions and can start their operations upon receipt of signals from the liquid transfer pumps. On the other hand, if the autosampler 102 is not in the state of waiting for the synchronization signals, their operations are not started at this timing and the autosampler will receive synchronization signals at the next time or later.

According to the above-mentioned flow, if the liquid transfer pressure obtaining interval of the liquid transfer pump overlaps the timing at which the above-mentioned sample injecting operation or the passage switching operation is done, the liquid transfer pump may change the liquid transfer velocity on the basis of the pressure changed temporarily by such operations. Thus, proper analysis results may not be obtained in some cases.

To eliminate such a disadvantage, the following technology is described in the embodiment of the present invention. Control is exercised so that the liquid transfer cycle of the liquid transfer pump driven by liquid transfer pressure may be synchronized with the sample injecting operation of the autosampler. In addition, the sample injecting operation is done at a timing rather than an interval in which the liquid transfer pressure of the liquid transfer pump is obtained.

The above-mentioned embodiment includes (1) a case of controlling the operation timings on the basis of the operation of the liquid transfer pump; (2) a case of controlling the operation timings on the basis of the operation of the autosampler; and (3) a case of controlling the operation timings of the respective functions on the basis of information stored in the data processing unit. Such cases are described below.

First Embodiment

Figure 3:
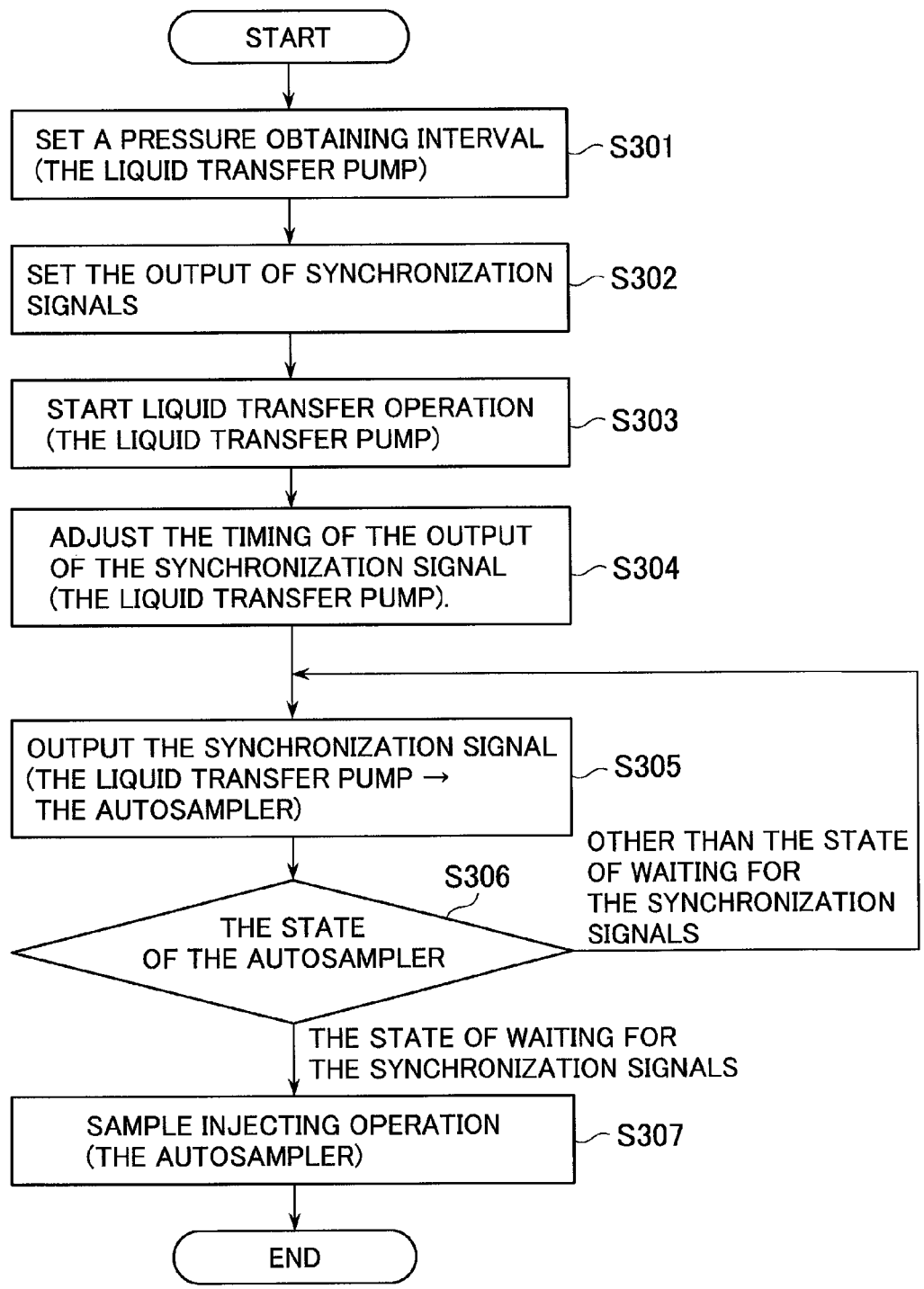
FIG. 3 is an operation flowchart for adjusting the timing of starting sample injecting operation with the liquid transfer pump according to the embodiment of the present invention.
Figure 4:
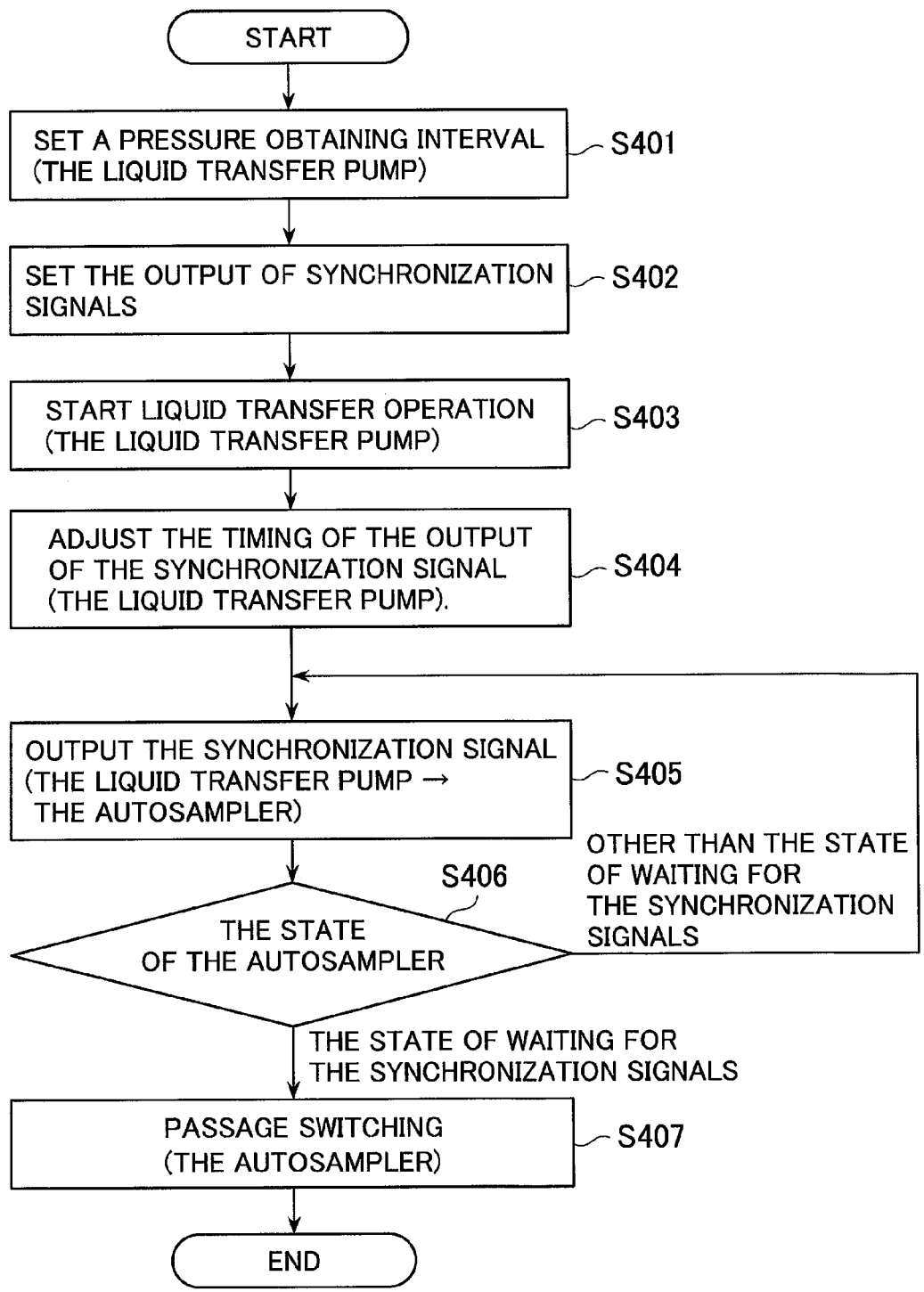
FIG. 4 is an operation flowchart for adjusting a timing of starting passage switching operation with the liquid transfer pump according to the embodiment of the present invention.

A first embodiment is described in which the operation timings are controlled on the basis of the operation of the liquid transfer pump with reference to FIGS. 3 and 4.

FIG. 3 is a flowchart for adjusting the timing of the start of liquid injecting operation by the liquid transfer pump according to the embodiment of the present invention.

The liquid transfer pumps 101A, 101B need to obtain from respective sensors liquid transfer pressures used for drive control. An interval is set in which pressure data is not taken in for a given length of time (S301).

This interval is set at greater than the period in which the pressure of the transferred liquid varies due to the sample injecting operation from the liquid transfer pumps 101A and 101B or passage switching operation by the autosampler 102.

The output of synchronization signals from the liquid transfer pumps 101A and 101B is set so as to control functions which include the injecting operation and passage switching operation of the autosampler 102 (S302). In this way, the liquid transfer cycle of the liquid transfer pump 101 is synchronized with the analysis cycle of an analysis unit including the autosampler 102. This causes the noise of the liquid transfer pump 101 at the same number of times and the same timing in one analysis. The influence of the noise of the liquid transfer pump 101 during the analysis is made constant. Thus, reproducibility of analysis can be improved.

After the above items have been set, the liquid transfer operations of the liquid transfer pumps 101A and 101B are started (S303).

The liquid transfer pumps 101A and 101B adjust a timing at which the synchronization signals are outputted to the autosampler 102 on the basis of information on the interval for obtaining liquid transfer pressure (S304). More specifically, when the synchronization signals are outputted while being matched with the liquid transfer cycle, the sample injecting operation of the autosampler 102 is made not to overlap the interval for obtaining liquid transfer pressure, that is, such a case is excluded from the timing of the output of the synchronization signals.

After the above-mentioned adjustment, the synchronization signal is outputted to the autosampler 102 on the basis of the liquid transfer cycle of one (e.g., a pump having a higher flow rate), of the liquid transfer pumps 101A and 101B, which is to be synchronized with the analysis cycle (S305).

If the autosampler 102 is here in the state of waiting for the synchronization signal (S306), the autosampler 102 implements the sample injecting operation on the basis of the signal outputted from the pump as described above (S307). On the other hand, if the autosampler 102 is not in the state of waiting for the synchronization signal, then the autosampler 102 does not start the sample injecting operation but will receive the synchronization signal at the next time or later.

As described above, the sample injecting operation of the autosampler 102 is synchronized with the operation of the liquid transfer pump 101. This can improve reproducibility of analysis as described above. In addition, the synchronization signal of the liquid transfer pump 101 is outputted so that the timing at which the sample injecting operation of the autosampler 102 is done may not overlap the interval for obtaining the liquid transfer pressure data. This can reduce the influence of the pressure variation on the drive control of the liquid transfer pump 101. Thus, both the reproducibility with a high degree of analysis accuracy and the accuracy of liquid transfer control can be obtained.

FIG. 4 is an operation flowchart for adjusting a passage switching timing by the liquid transfer pump according to the embodiment of the present invention. The flowchart of FIG. 4 is different from that of FIG. 3 in that the operation of the autosampler 102 is done depending on whether or not the autosampler is in the state of waiting for passage switching (S406 and S407).

According to the present embodiment, the liquid transfer pump can control a timing for obtaining liquid transfer pressure in drive control of the liquid transfer pump per se, and for starting the sample injecting operation, passage switching of the autosampler 102, and other functions. Therefore, it is not necessary to depend on other modules for storing information on the control of a liquid transfer device other than the synchronization signal. Thus, the scope of application to the other modules can be increased.

Second Embodiment

Figure 5:
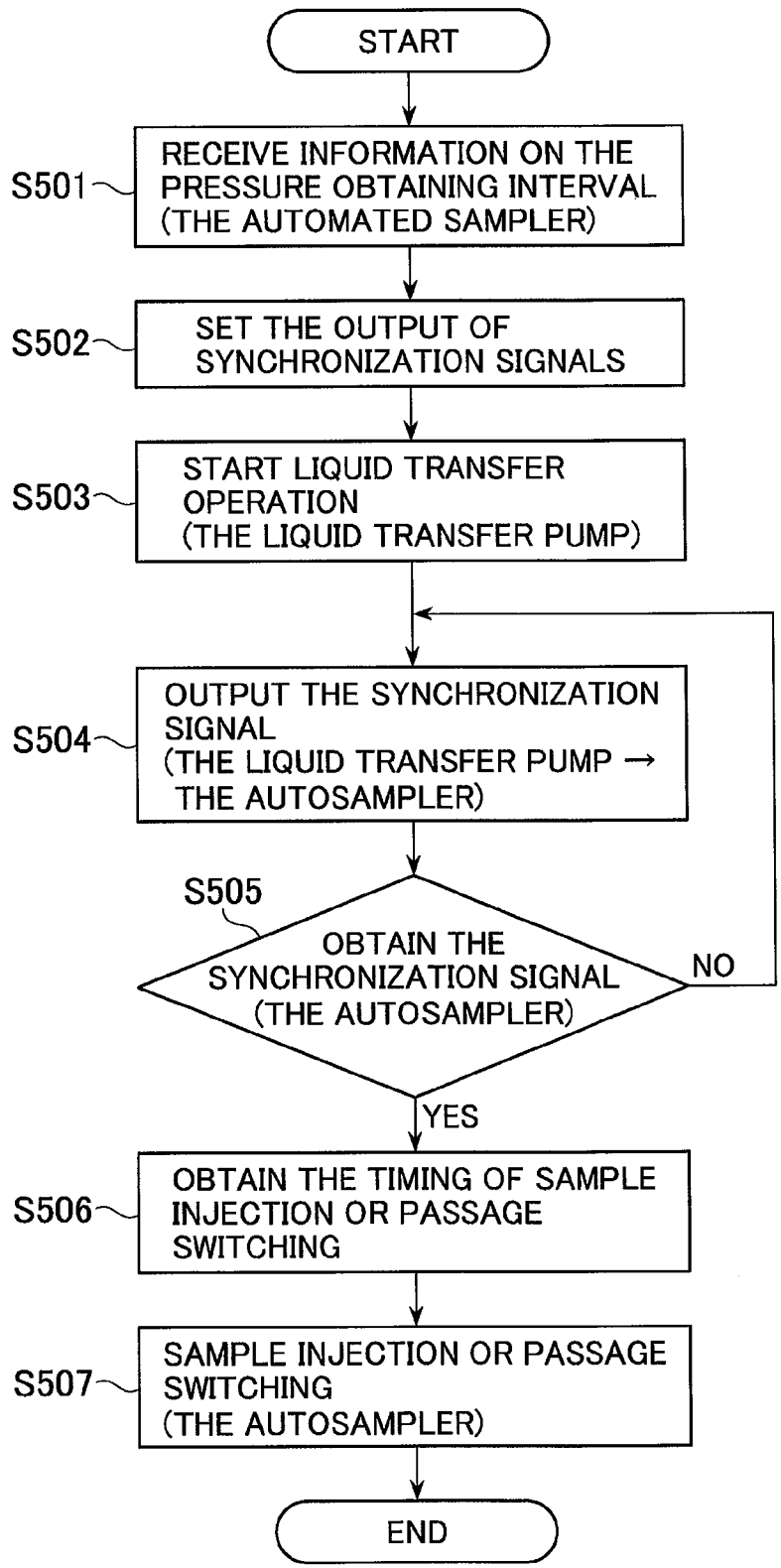
FIG. 5 is an operation flowchart for determining a timing at which sample injecting or passage switching operation is started with the autosampler according to an embodiment of the present invention.

A second embodiment is described in which the timings of various operations are controlled on the basis of the operation of the autosampler with reference to FIG. 5.

FIG. 5 illustrates an operation flowchart for adjusting the timings of the sample injecting operation and passage switching operation of the autosampler according to the second embodiment of the present invention.

The autosampler 102 first receives information on an interval for obtaining liquid transfer pressure from the liquid transfer pump 101 (S501).

The output of synchronization signals from the liquid transfer pumps 101A and 101B are set so as to control functions including the sample injecting operation and passage switching operation of the autosampler 102 (S502).

After the setting of the above-mentioned items, the liquid transfer pumps 101A and 101B start liquid transfer operation (S503).

Unlike the first embodiment, the liquid transfer pumps 101A and 101B are driven at a fixed cycle. Specifically, the liquid transfer pumps 101A and 101B output synchronization signals to the autosampler 102 at a determined control phase position and at a liquid transfer cycle of one (e.g., a pump having a higher flow rate) of the liquid transfer pumps which is synchronized with an analysis cycle regardless of the interval for obtaining liquid transfer pressure (S504).

The autosampler 102 obtains the synchronization signal if its own state upon receipt of the synchronization signal is a state of waiting for the synchronization signal (S505). On the other hand, if its own state is not the state of waiting for the synchronization signal, the autosampler 102 prepares for the next output timing without obtaining the synchronization signal at this timing.

On the basis of the synchronization signal thus obtained and the information on an pressure obtaining interval, the autosampler 102 brings the sample injecting operation or the passage switching operation to the same position as the control phase of the liquid transfer pump 101 and obtains the timing not overlapping the pressure obtaining interval (S506). Then, the autosampler 102 implements the sample injecting operation or the passage switching operation at the timing thus obtained (S507).

According to the above-mentioned flow, while maintaining the reproducibility of analysis, the analysis can be implemented without reflecting the influence of the operation of the autosampler 102 on liquid transfer, on the control of the liquid transfer pump 101.

According to the present embodiment, after the autosampler 102 has once received the information on the interval for obtaining liquid transfer pressure and the synchronization signal from the liquid transfer pump, the autosampler 102 can adjust the timing of the sample injecting operation or the passage switching timing without being restricted by other units.

Third Embodiment

Figure 6:
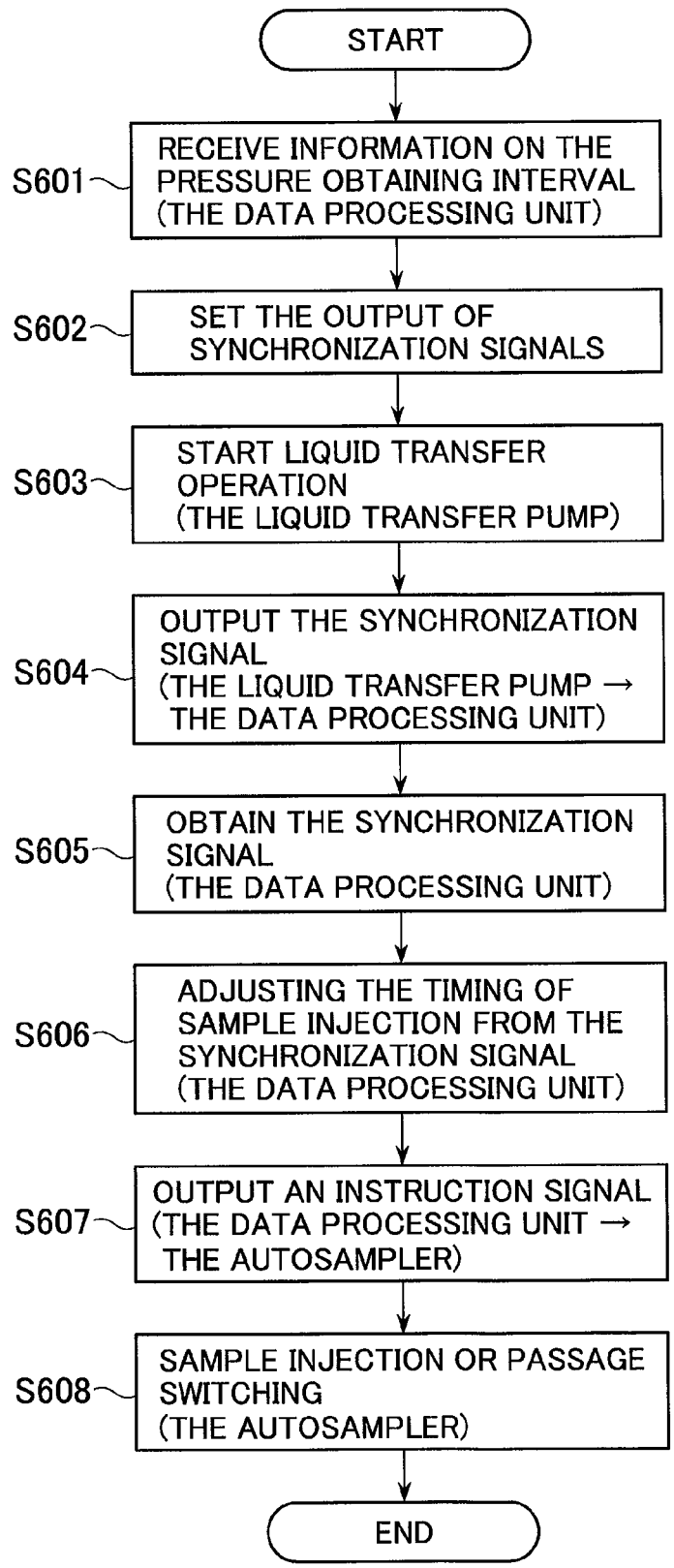
FIG. 6 is an operation flowchart for determining a timing at which the data processing unit controls the start of sample injecting or passage switching operation according to an embodiment of the present invention.

A third embodiment is described in which the data processing unit controls the various operation timings of the liquid transfer pump and the autosampler with reference to FIG. 6.

The data processing unit 105 first receives information on an interval for obtaining liquid transfer pressure from the liquid transfer pump 101 (S601).

The data processing unit 105 next sets the output of synchronization signals from the liquid transfer pumps 101A and 101B so as to control functions including the sample injecting operation and passage switching operation of the autosampler 102 (S602).

After the above-mentioned setting, the liquid transfer pumps 101A and 101B start liquid transfer operation (S603).

Unlike the first embodiment, the liquid transfer pumps 101A and 101B are driven at a fixed cycle. Specifically, the liquid transfer pumps 101A and 101B output synchronization signals to the data processing unit 105 at a position where a control phase is determined in a liquid transfer cycle of one of the liquid transfer pumps which is synchronized with an analysis cycle regardless of the interval for obtaining liquid transfer pressure (S604).

The data processing unit 105 obtains the synchronization signals thus outputted from the liquid transfer pumps (S605). Then, on the basis of the synchronization signals thus obtained and the information on the pressure obtaining interval, the data processing unit 101 brings the sample injecting operation or the passage switching operation of the autosampler 102 to the same position as the control phase of the liquid transfer pump 101. In addition, the data processing unit 101 obtains the timing which does not overlap the pressure obtaining interval and at which the autosampler 102 is in a state of waiting for an instruction signal (S606). Then, the data processing unit 105 sends an instruction to the autosampler 102 to implement the above-mentioned operation at the timing thus obtained (S607).

The autosampler 102 implements the sample injecting operation or the passage switching on the basis of the signal outputted from the data processing unit 105 (S608).

According to the above-mentioned flow, while maintaining the reproducibility of analysis, the analysis can be implemented without reflecting the influence of the operation of the autosampler 102 on liquid transfer, on the control of the liquid transfer pump 101.

Figure 11:
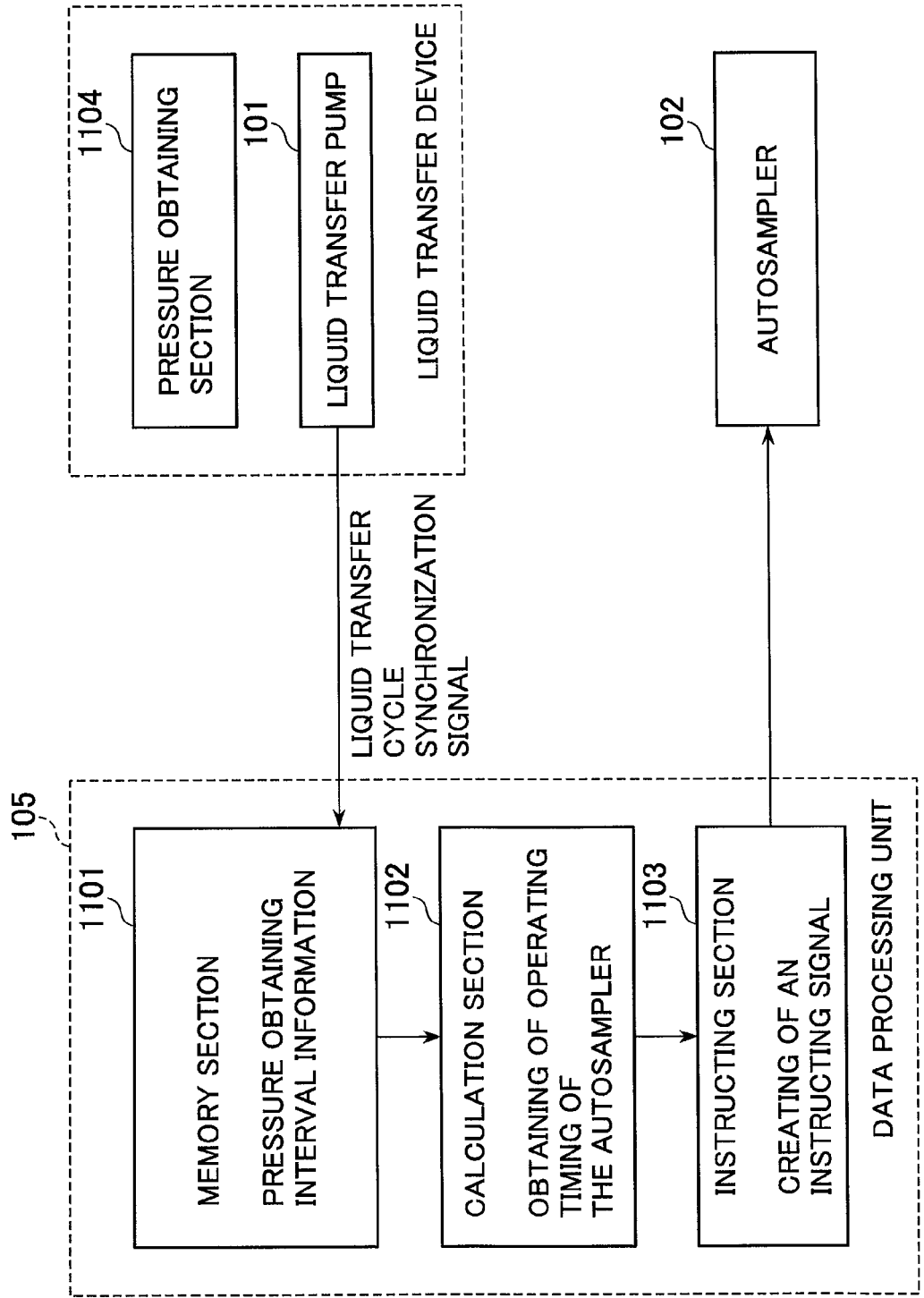
FIG. 11 illustrates the schematic internal configuration of a data processing unit which exercises control according to a third embodiment of the present invention.

FIG. 11 is a schematic diagram of the data processing unit 105, illustrating operating functions according to the present embodiment.

Referring to FIG. 11, the data processing unit 105 obtains information on a liquid transfer cycle from the liquid transfer pump 101 and stores the information in a memory section 1101. The memory section 1101 not only can previously store information on a pressure obtaining interval therein from a pressure obtaining section 1104 as shown in the figure but also can receive and store therein the information from the pressure obtaining section 1104.

On the basis of the information stored in the memory section 1101, a calculation section 1102 obtains a particular timing at which the autosampler 102 starts operation. This timing is synchronized with the liquid transfer cycle of the liquid transfer pump 101 and does not overlap the pressure obtaining interval.

An instruction section 103 creates and supplies an instruction signal to the autosampler 102 so that the autosampler 102 starts operation at the timing obtained by the calculation section 1102.

According to the present embodiment, the data processing unit 105 manages the conditions of the overall system. Therefore, even if a plurality of the liquid transfer pumps 101A and 101B are driven at respective different control phases, the data processing unit 105 can give an instruction to the autosampler 102 to implement the sample injecting operation or the passage switching while excluding the interval for exercising the pressure control on the liquid transfer pump 101. The most pressure-stable intervals of the liquid transfer pumps 101A and 101B may not overlap each other depending on a difference in control phase between the liquid transfer pumps 101A and 101B. In such a case, the data processing unit 105 exercises control while matching with the pump having the highest flow rate. In this way, the influence on liquid transfer control is reduced to keep the reproducibility of analysis.

Further, in the first to third embodiments, the point of starting analysis data collection is set at a point not after the sample injecting operation of the autosampler 102 but at the synchronization signal outputted from the liquid transfer pump 101. This can prevent the problem in that because of improved liquid transfer velocity, a sample to be analyzed may already reach the detecting section at the time of collecting data.

In this case, the data processing unit 105 obtains the output signal from the liquid transfer pump 101 and exercises control to start the collection of analysis data.

What is claimed is:

1. A liquid chromatograph apparatus comprising:
    a liquid transfer section including a liquid transfer pump for transferring liquid and a pressure obtaining section for obtaining the pressure of the liquid being transferred;
    an autosampler for injecting a sample into a passage in which the transferred liquid flows and switching the passage; and
    a control section for controlling an amount of the transferred liquid on the basis of the obtained pressure, wherein
    the control section controls the autosampler so that
        a liquid transfer cycle of the liquid transfer pump and operation of the autosampler will be synchronized with each other, and
        the operation of the autosampler will be implemented at a timing rather than an interval in which the liquid pressure is obtained by the pressure obtaining section, so as to prevent an overlap between a sample injecting operation of the autosampler and the interval in which the liquid pressure is obtained by the pressure obtaining section.

2. The liquid chromatograph apparatus according to claim 1, wherein
    on the basis of information on the liquid transfer cycle sent from the liquid transfer pump and on the pressure obtaining interval obtained by the pressure obtaining section, the control section supplies a control signal to the autosampler so that
        the liquid transfer cycle and the operation of the autosampler will be synchronized with each other, and
        the operation of the autosampler will be implemented at a timing rather than the interval in which the liquid pressure is obtained by the pressure obtaining section.

3. The liquid chromatograph apparatus according to claim 1, wherein
    the liquid transfer pump has at least one liquid transfer cycle,
    the liquid transfer pump supplies a synchronization signal to the control section at a predetermined timing of the liquid transfer cycle,
    on the basis of information on the liquid transfer cycle of the liquid transfer pump and on the pressure obtaining interval obtained by the pressure obtaining section, the control section obtains an operation starting time so that
        the liquid transfer cycle and the operation of the autosampler will be synchronized, and
        the operation of the autosampler will be implemented at a timing rather than the interval in which the liquid pressure is obtained by the pressure obtaining section, and
    the control section supplies a control signal to the autosampler so that the autosampler will start operation when the operation starting time comes after the synchronization signal was supplied by the liquid transfer pump.

4. The liquid chromatograph apparatus according to claim 1, wherein the control section includes:
    a memory section for storing information on the liquid transfer cycle sent from the liquid transfer pump and on the interval in which the pressure is obtained by the pressure obtaining section;
    a calculation section for obtaining, on the basis of the stored information, a timing which is synchronized with the liquid transfer cycle rather than the pressure obtaining interval; and
    an instructing section for supplying an instructing signal so as to implement the operation of the autosampler at the obtained timing.

5. An analytical system using a liquid chromatograph apparatus, the liquid chromatograph apparatus comprising:
    a liquid transfer section including a liquid transfer pump for transferring liquid and a pressure obtaining section for obtaining the pressure of the liquid being transferred;
    an autosampler for injecting a sample into a passage in which the transferred liquid flows and switching the passage; and
    a control section for controlling an amount of the transferred liquid on the basis of the obtained pressure, wherein
    the control section controls the autosampler so that
        a liquid transfer cycle of the liquid transfer section and operation of the autosampler will be synchronized with each other, and
        the operation of the autosampler will be implemented at a timing rather than an interval in which the liquid pressure is obtained by the pressure obtaining section, so as to prevent an overlap between a sample injecting operation of the autosampler and the interval in which the liquid pressure is obtained by the pressure obtaining section.

6. The analytic system according to claim 5, wherein
    on the basis of information on the liquid transfer cycle sent from the liquid transfer section and on the pressure obtaining interval obtained by the pressure obtaining section, the control section supplies a control signal to the autosampler so that
        the liquid transfer cycle and the operation of the autosampler will be synchronized with each other, and
        the operation of the autosampler will be implemented at a timing rather than the interval in which the liquid pressure is obtained by the pressure obtaining section.

7. The analytic system according to claim 5, wherein
    the liquid transfer pump has at least one liquid transfer cycle,
    the liquid transfer pump supplies a synchronization signal to the control section at a predetermined timing of the liquid transfer cycle,
    on the basis of information on the liquid transfer cycle of the liquid transfer pump and on the pressure obtaining interval obtained by the pressure obtaining section, the control section obtains an operation starting time so that the operation of the autosampler will be implemented at a timing rather than the interval in which the liquid pressure is obtained by the pressure obtaining section, and the control section supplies a control signal to the autosampler so that the autosampler will start operation when the operation starting time comes after the synchronization signal was supplied by the liquid transfer pump.

8. The analytic system according to claim 5, wherein the control section includes:
a memory section for storing information on the liquid transfer cycle sent from the liquid transfer pump and on the interval in which the pressure is obtained by the pressure obtaining section;
a calculation section for obtaining, on the basis of the stored information, a timing which is synchronized with the liquid transfer cycle rather than the pressure obtaining interval; and
an instructing section for supplying an instructing signal so as to implement the operation of the autosampler at the obtained timing.

9. A liquid chromatograph apparatus comprising:
a liquid transfer section including a liquid transfer pump for transferring liquid and a pressure obtaining section for obtaining the pressure of the liquid being transferred;
an autosampler for injecting a sample into a passage in which the transferred liquid flows and switching the passage; and
a control section for controlling an amount of the transferred liquid on the basis of the obtained pressure, wherein
the control section controls the autosampler so that
a liquid transfer cycle of the liquid transfer pump and operation of the autosampler will be synchronized with each other, and
the operation of the autosampler will be implemented at a timing rather than an interval in which the liquid pressure is obtained by the pressure obtaining section;
wherein the liquid transfer pump has at least one liquid transfer cycle,
wherein the liquid transfer pump supplies a synchronization signal to the control section at a predetermined timing of the liquid transfer cycle,
wherein on the basis of information on the liquid transfer cycle of the liquid transfer pump and on the pressure obtaining interval obtained by the pressure obtaining section, the control section obtains an operation starting time so that
the liquid transfer cycle and the operation of the autosampler will be synchronized, and
the operation of the autosampler will be implemented at a timing rather than the interval in which the liquid pressure is obtained by the pressure obtaining section, and
wherein the control section supplies a control signal to the autosampler so that the autosampler will start operation when the operation starting time comes after the synchronization signal was supplied by the liquid transfer pump.

10. The liquid chromatograph apparatus according to claim 9, wherein
on the basis of information on the liquid transfer cycle sent from the liquid transfer pump and on the pressure obtaining interval obtained by the pressure obtaining section, the control section supplies a control signal to the autosampler so that
the liquid transfer cycle and the operation of the autosampler will be synchronized with each other, and
the operation of the autosampler will be implemented at a timing rather than the interval in which the liquid pressure is obtained by the pressure obtaining section.

11. The liquid chromatograph apparatus according to claim 9, wherein the control section includes:
a memory section for storing information on the liquid transfer cycle sent from the liquid transfer pump and on the interval in which the pressure is obtained by the pressure obtaining section;
a calculation section for obtaining, on the basis of the stored information, a timing which is synchronized with the liquid transfer cycle rather than the pressure obtaining interval; and
an instructing section for supplying an instructing signal so as to implement the operation of the autosampler at the obtained timing.

* * * * *